United States Patent [19]

Moll et al.

[11] Patent Number: 4,547,070

[45] Date of Patent: Oct. 15, 1985

[54] APPARATUS AND PROCESS FOR MEASURING THE COLLOIDAL STABILITY OF LIQUIDS

[75] Inventors: Manfred Moll, Flavigny sur Moselle; Daniel Bazard, Custines; Michel Niclause, Nancy; Louis-Marie Vincent, Seichamps; Jean-Claude Andre, Nancy, all of France

[73] Assignee: Centre de Recherche et de Development, Champigneulles, France

[21] Appl. No.: 246,952

[22] Filed: Mar. 24, 1981

[30] Foreign Application Priority Data

Mar. 24, 1980 [FR] France ................. 80 06464

[51] Int. Cl.$^4$ ........................................... G01N 21/00
[52] U.S. Cl. ..................................... 356/339; 356/36
[58] Field of Search .................. 356/339, 341, 343, 36; 235/241, 808

[56] References Cited

U.S. PATENT DOCUMENTS

| | | | |
|---|---|---|---|
| 3,561,825 | 2/1971 | Ried, Jr. et al. | 356/341 X |
| 3,617,222 | 11/1921 | Matte | 356/339 X |
| 4,043,669 | 8/1977 | Gehatia et al. | 356/341 X |
| 4,047,815 | 9/1977 | Sedlacek | 356/343 X |
| 4,053,229 | 10/1977 | McCluney | 356/339 X |

OTHER PUBLICATIONS

Korableva et al., "Installation for the Measurement of Scattering and Depolarization of Light by a Liquid", *Pribory i Tekhnika Eksperimenta*, No. 4, pp. 223-225, 8/78.

Primary Examiner—William L. Sikes
Assistant Examiner—Matthew W. Koren

[57] ABSTRACT

Apparatus for measuring the colloidal stability of liquids comprising a sample-holder containing a sample of the liquid the turbidity of which is to be measured, a cooling tank containing the sample-holder and associated with a cooling unit, a laser light source of appropriate wavelength, a photopile for measuring the light flux diffused through the sample to be checked, a reference photopile for permanently controlling the exciting beam, a semitransparent mirror reflecting a part of the light beam in the direction of the reference photopile, a device for absorbing the nondiffused light and a logic system associated with a microprocessor for calculating the value of the turbidity of the sample.

13 Claims, 6 Drawing Figures

APPARATUS AND PROCESS FOR MEASURING THE COLLOIDAL STABILITY OF LIQUIDS

BACKGROUND OF THE INVENTION

The present invention relates to a novel apparatus and process for measuring with great accuracy and great rapidity the colloidal stability of liquids, and particularly nutritious liquids of the beer,wine,oil type.

Measuremenat of the turbidity of nutritious liquids, when cold, is of great importance in that it has enabled, and still enables at the present time, the improvement of the colloidal stability of beers, wines and other drinks obtained by fermentation, or gaseous drinks, as well as the limpidity of oils when cold.

In particular insofar as the measurement of the turbidity of cold beers is concerned, the first tests proposed measured the tendency to the formation of turbidity in beers while maintaining the beers being tested for 7 days at a temperature of 40° C., then for 24 hours at a temperature of 0° C. (EBC test) Extracted from the statistical study of the results thus obtained was a correlation between the values found by the EBC tests and the sparkle of the beer after 6 months storage at ambient temperature, with a highly significant coefficient.

The EBC tests, lasting 8 days, presented however the major disadvantage of their length and very often they could only be carried out after the beer had left the brewery when no correction could obviously be made to the treatment of the beer. An important improvement was made to the measurement of the turbidity of cold beers, by L. CHAPON and M. CHEMARDIN (see EBC Proceeding 1967, Madrid, p. 389-405) by means of the "alcohol-cold" test which enables the development of the turbidity of the beer at −8° C. for 40 minutes, by adding thereto from 0 to 6% of ethanol. The principle of this test makes use of the ethanol enrichment of the beer to cause therein the formation of turbidity when cold. Through its hydroxyl group, ethanol may play the role of proton donor and is associated, by hydrogen bonds, with the peptidic groups of the protein part of the protein-tannin associations which form the particles of the turbidity when cold, driving out their solvation water molecules, and thus reducing their solubility. This reduction of solubility is all the more marked the lower with temperatures of beer. The apparatus for the cold measurement of turbidity perfected by L. CHAPON and M. CHEMARDIN (see above quotation) comprised a nephelometer refrigerated by means of a Peltier element to a constant temperature between −8° and +20° C., a light source formed by a 30 W lamp supplied with a voltage of 6 V, cells for measuring the diffused light formed by barrier-layer cells, a current detector formed by a galvanometer, a recorder formed by a Sefram spot-follower and a potentiometric recorder for recording turbidity curves as a function of the temperature. Calibration of the nephelometer was achieved by means of formazine solutions. This apparatus has been perfected by the Applicant (see French Patent TEPRAL No. 73 09798 of Mar. 12, 1973).

A large number of apparatuses, like the CHAPON and CHEMARDIN apparatus, which rely on the measurement of light diffused at different angles, have been proposed in the prior art. They do not allow however absolute determination of the turbidity, for they cannot take into account the microscopic nature of the turbidity of beer, which is formed by particles of varying size, and which has been established by electronic microscopy as being between 0.1 and 1 micron so that the precise determination of the turbidity of beer requires measuring methods and apparatuses which take into account the size of the particles. From this new point of view, KLINE and AXILROD have proposed an apparatus for the photoelectric determination of turbidity, formed by a photoelectric colorimeter in which two transmission readings are carried out (at 440 nm in a tank of 5 cm diameter or at 580 nm in a tank of 20 mm diameter), at about 10 cm from the photoelectric cell. The readings are then converted into optical densities and the difference between these values depend on the total light diffused and represent the measurement of the turbidity. CLEASSON and SANDEGREN have also proposed associating, for the measurement of cold turbidity, the dispersion of the light and electronic microscopy. The same Authors have developed an apparatus for measuring the size of the particles by Doppler effect, by measuring the difference between the emission wavelength of a laser on a turbidity sample and that of the diffused light, to deduce therefrom the speed of the particles, then their size.

Furthermore, there has been proposed (see J. E. CAUPEIL, Unilever Research, "Revue Francaise des Corps Gras", No. 8-9 August-September 1977, p. 427-431) an apparatus for the rapid measurement of the limpidity of oils, by laser. This apparatus comprises,: a pump which causes the oil sample to be checked to flow through a spiral bathed in an oil bath brought up to 100° C., then through a first measuring cell, then through a spiral placed in melting ice, then finally through a second measuring cell; two laser light sources; two microscopes placed in front, which serve for visual observation; two microscopes placed in the rear, which serve to form an enlarged image of the laser ray on a diaphragm placed in front of the corresponding detector; and two detectors each formed by an electron photomultiplying tube (EPT) which transforms the light signal into an electric current, which is transformed into a potential difference by a potentiometric recorder. The number of mV read after the first measurement, made after heating to 100° C., is subtracted from the number of mV read after the second measurement, made after cooling to 0° C. The difference obtained from the two readings made on the recorder is the measurement of the quantity of crystals present in the oil, whose concentration is read from a standard curve. The measurement operation is carried out within 15 minutes, whereas the cold tests previously used lasted several days.

SUMMARY OF THE INVENTION

The aim of the present invention is to provide an apparatus for measuring the colloidal stability of liquids, particularly nutritious liquids, by means of laser light, in which it is possible to use the "alcohol-cold" test developed by CHAPON and CHEMARDIN, within a period of time which is considerably reduced with resect to the conditions established by these Authors. However, the known apparatus using laser light for measuring the colloidal stability of beers is essentially a counting apparatus which compares two wavelengths, i.e. the emission wavelength of the laser light with that of the diffused light, and the apparatus for measuring the limpidity of oils by laser aims at measuring the intensity of the light diffused by the microcrystals of waxes passing through the laser ray, which results in the emission of light signals whose frequency depends on the particle concentration, which signals are transformed by the EPT into an electric current, itself transformed into a potential difference which represents the microcrystal concentration of the oil. The apparatus in accordance with the present invention in contrast is based on the principle of the simultaneous measurement of the exciting light flux and of the diffused light flux, by eliminating the intensity fluctuations of the laser, and obtaining the value of the turbidity from the relationship between these two measurements.

The present invention provides an apparatus for measuring the colloidal stability of liquids such as nutritious liquids, for example beers, wines and other drinks obtained by fermentation, or gaseous drinks, and oils, in particular, by measuring the diffusion of the light emitted by a laser ray, characterized in that it comprises essentially, in combination, a sample-holder carrying at least one cell containing a sample of the liquid whose turbidity, when the liquid is cold, it is desired to measure; a cooling tank brought to a constant cooling temperature, adjustable to 1/10th of a degree, in which is contained the sample-holder and which is associated with a cooling unit of appropriate type; a light source formed by a laser ray of appropriate wavelength; a photopile for analysing and measuring the light flux from the laser light source, diffused through the sample to be checked; a reference photopile for permanently controlling the intensity of the exciting beam; a semi-transparent mirror for reflecting a part of the exciting light beam emitted by the laser ray, in the direction of the reference photopile; a device for absorbing the non-diffused light; a logic system associated with a microprocessor for calculating the relationship between the measurements effected by the two photopiles for obtaining the value of the turbidity of the sample obtained after a period of time which depends on the temperature of the cooling tank and, after a few minutes, with respect to the initial sparkle, for comparing said value with the standard value obtained with a formazine solution and displaying the results in formazine units (UF), for recording the turbidity curve of the sample as a function of the check time and for possible control of the apparatus and storage of the results obtained.

The apparatus in accordance with the present invention which comprises essentially, in combination, a refrigerated element containing samples to be checked, an optical system for diffusing the light emitted by a laser radiating source and for measuring the diffusion of the light, and a logic system for converting said light flux measurements into voltage current, for measuring the variations of said voltage current, for recording said variations, for comparing with a standard curve stored in the memory, for recording the data obtained and displaying in standard units, is furthermore characterized by the following arrangements:

In accordance with the invention, the laser light source is formed by a helium-neon laser in appropriate proportions for emitting a wavelength of 6328 Å at which the light flux presents very great stability and low divergence which reduces considerably the proportion of parasite light of the apparatus.

The choice of a laser excitation source emitting at 6328 Å presents furthermore the advantage of avoiding interferences, considering that the compounds present in beer other than the turbidity particles when cold, do not absorb at the emission wavelength of the laser.

According to an advantageous embodiment of the invention, the photopiles are disposed at an angle of 90° with respect to the emitted light.

According to another advantageous embodiment of the invention, the photopiles are designed to operate at a low voltage and low current, respectively of the order of 50 mV and 0.66 mA, and each comprise two integrated operational amplifier stages of which the first is mounted as a "current-voltage" converter which delivers a current proportional to the exciting flux, at said low voltage, and the second stage of which is formed by an integrated circuit connected as a normal voltage amplifier, the outputs of the two amplifiers feeding into a measuring apparatus, through a resistance network giving a 50 mV standard for the total deviation, into an output for recording through a resistance network and into an input of an analog-digital converter, through an amplitude-limiting circuit which ensures protection of said converter and which is advantageously formed by a resistor and a zener diode.

According to yet another advantageous embodiment of the apparatus of the invention, it is provided with a system for supplying the sample-holder with samples, advantageously formed by a feed-regulating device, such as a programmed automatically controlled peristaltic pump, which takes the liquid from a storage tank or directly from the manufacturing tanks, and transfers it to the cells of the sample-holder, in desired proportions.

Also in accordance with the invention, the apparatus is provided with a system for introducing ethanol into the liquid to be tested before introduction thereof into the sample-holder cells, advantageously formed by a feed-regulating device such as a programmed automatically controlled peristaltic pump with electromagnetic valve, which takes the ethanol contained in a storage tank associated with the apparatus of the invention, and introduces it into the liquid in desired proportions.

According to an advantageous embodiment of the apparatus in accordance with the invention, the programmed automatic introduction of the samples of liquid to be checked and of ethanol into the cells of the sample-holder is achieved with the help of the above-mentioned microprocessor.

According to another advantageous embodiment of the apparatus in accordance with the present invention, it comprises means for adjusting the sensitivity of the measurement, controlled automatically and programmed by the microprocessor and advantageously formed by load resistors.

According to an advantageous arrangement of the invention, the apparatus is furthermore equipped with a circuit for the flow of liquids for cleaning the cooling tank and the sample-holder cells, controlled and programmed by the microprocessor.

The present invention also provides a method for measuring the colloidal stability of liquids, particularly nutritional liquids, and more particularly beers, characterized in that a lazer ray of 6328 Å wavelength is directed onto a beer sample whose turbidity when cold it is desired to check, an appropriate quantity of ethanol having been added to the sample, which may reach 12% by volume with respect to the volume of the beer, and cooled to a temperature of the order of −8° C. practically instantaneously on its entry into the apparatus, the capacity of the cell containing the sample being of the order of 150 µl, so as to obtain maximum turbidity after 15 minutes, the diffusion of the light flux of which ($S_1$) is measured by a photopile placed at 90° with respect to the emission direction of the laser ray, in the form of a light signal transformed into current-voltage by the photopile and transmitted to a microprocessor, a part of the light flux being reflected, by a semitransparent mirror, towards a reference photopile also placed at 90°, which measures simultaneously the intensity of the emitted light flux ($S_0$) and transmits the corresponding signal to the microprocessor which calculates the relationship $S_1/S_0$ so as to eliminate the fluctuations in intensity of the laser and display the value obtained which, after comparison with a standard curve established in a known way by means of a formazine solution and integrated by the microprocessor, is expressed directly in formazine units (UF), so that a sensitivity curve depending on the UF reading is established and recorded.

Besides the preceding arrangements, the invention comprises further arrangements which will become evident from the following description.

The present invention relates more particularly to apparatuses and processes for measuring the colloidal stability of liquids, particularly nutritional liquids, such as beers, wines and other drinks obtained by fermentation, or gaseous drinks, and oils, in particular, by laser, in accordance with the preceding arrangements, the means for their implementation and realization and general installations comprising said apparatuses and processes.

DESCRIPTION OF THE DRAWINGS

The invention will be better understood with the help of the complement of description which follows which refers to the accompanying drawings in which.

It will of course be readily understood that these drawings and the corresponding descriptive parts are given solely by way of illustration of the subject of the invention, of which they form in no wise a limitation.

DESCRIPTION OF THE PREFERRED EMBODIMENTS

Figure 1:
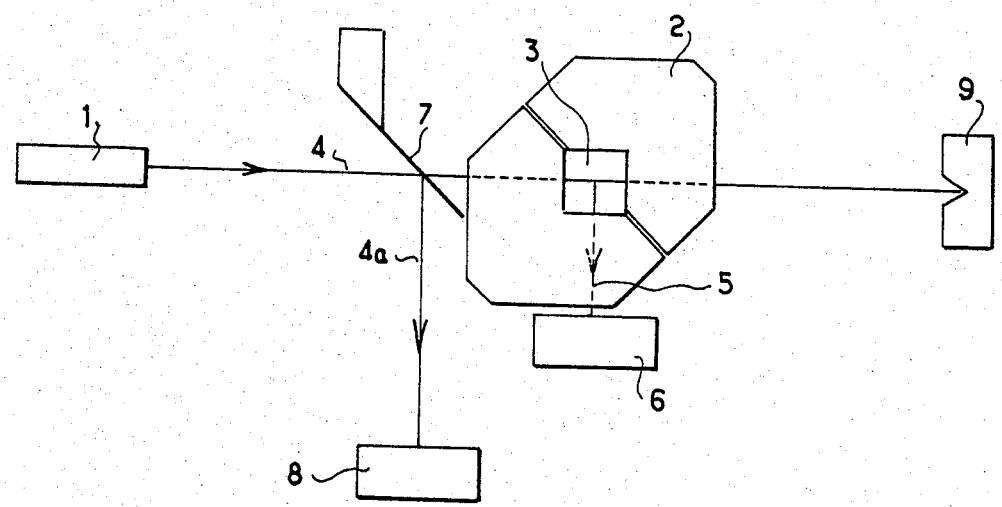
FIG. 1 is a schematical representation of the optical system for measuring the diffusion of a laser ray.
Figure 3:
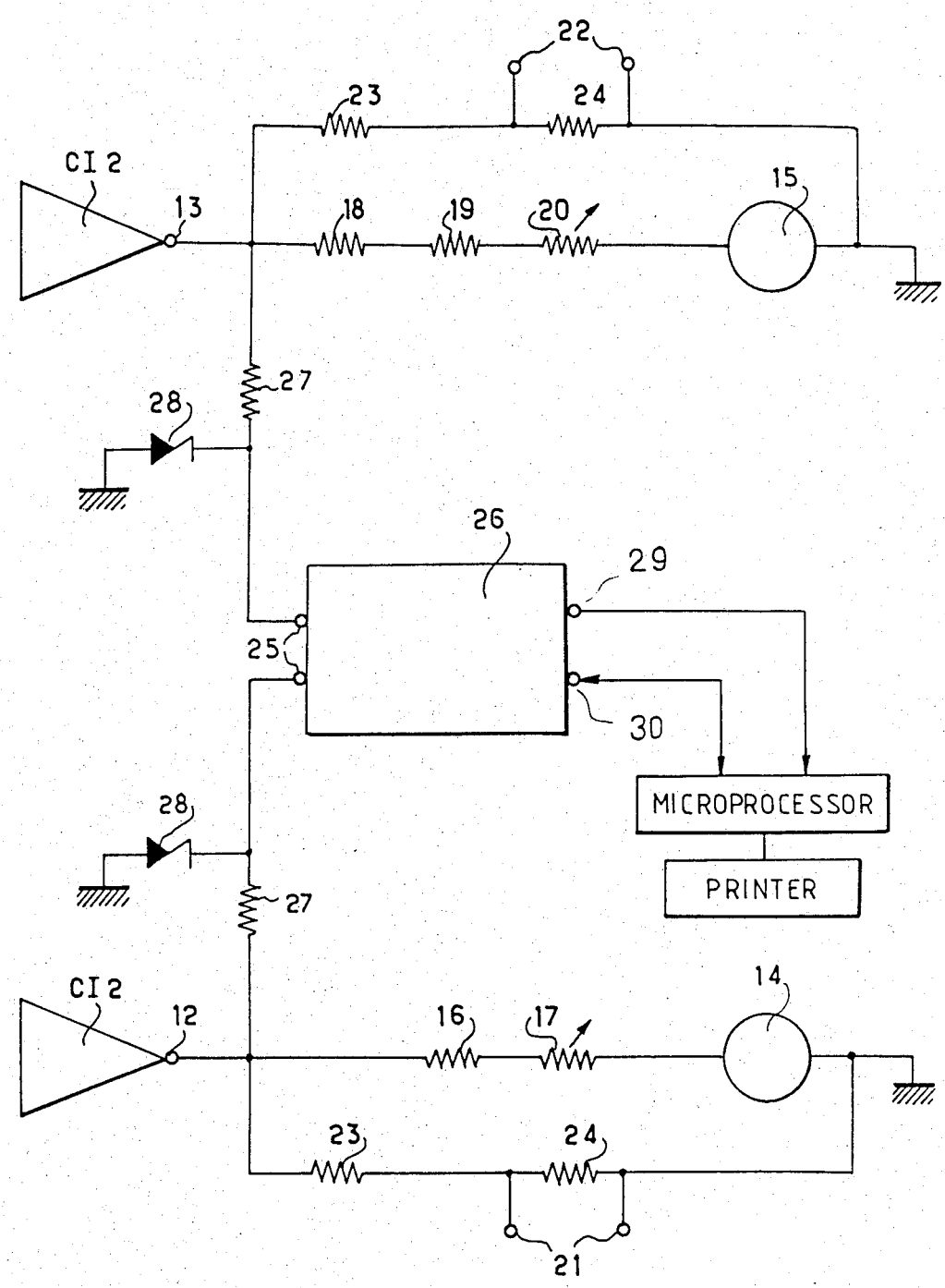
FIG. 3 is a diagram of the output circuits of the amplifiers of the photopiles.

The optical system for measuring the diffusion of the light emitted by a laser in accordance with the present invention comprises a helium-neon laser light source 1 emitting at a wavelength of 6328 Å, a cooling tank 2 associated with a cooling unit (not shown) and whose temperature is adjusted to within 1/10th of a degree by means of a thermostat (not shown), between −5° and −10° C. for example. Tank 2 may be designed either so as to form in itself a sample-holder cell receiving a sample of the liquid to be checked, the admission and removal to be controlled by the microprocessor which will be mentioned further on, or so as to receive a sample-holder carrying a plurality of cells in which appropriate quantities of samples to be checked are introduced, the analysis of which and the gathering of results being managed by the microprocessor. Tank 2 comprises windows, of which window 3 can be seen in FIG. 1, respectively for admitting into tank 2 the exciting light flux ($S_0$) 4 and for diffusing the diffused flux 5. The diffused flux ($S_1$) 5 is measured by a measuring photopile 6 which will be described in more detail further on, and which is placed at 90° with respect to the exciting flux 4. A part 4a of the exciting flux 4 is reflected by a semitransparent mirror 7, towards a reference photopile 8 which permanently controls the intensity of the exciting flux and which is also placed at 90° with respect to the exciting flux 4. The exciting flux $S_0$ and diffused flux $S_1$ are measured simultaneously by the two photopiles 6 and 8 and the corresponding measurements are sent in the form of signals $E_1$ and $E_2$ (see FIG. 3) to a microprocessor which calculates the relationship $S_1/S_0$ which eliminates the fluctuations in intensity of the laser and which displays the value obtained. A device for absorbing the non-diffused laser ray (such as Wood's horn 9) which reduces, in the sample-holder cell, the proportion of parasite light, is also added to the optical system of the invention shown schematically in FIG. 1.

The choice of a laser ray emitting at the wavelength of 6328 Å presents the advantage of eliminating the interferences due to the presence of other particles than the particles of the cold turbidity, so as to give rise to a light flux of great stability and to a beam with low divergence and, consequently, a low proportion of parasite light.

The photopiles 6 and 8 used for measuring the exciting flux ($S_0$) and diffused flux ($S_1$) give a good spectral response at 6328 Å and work at low voltages, which reduces the fatigue to which the measuring apparatus of the invention is subjected.

Figure 4:
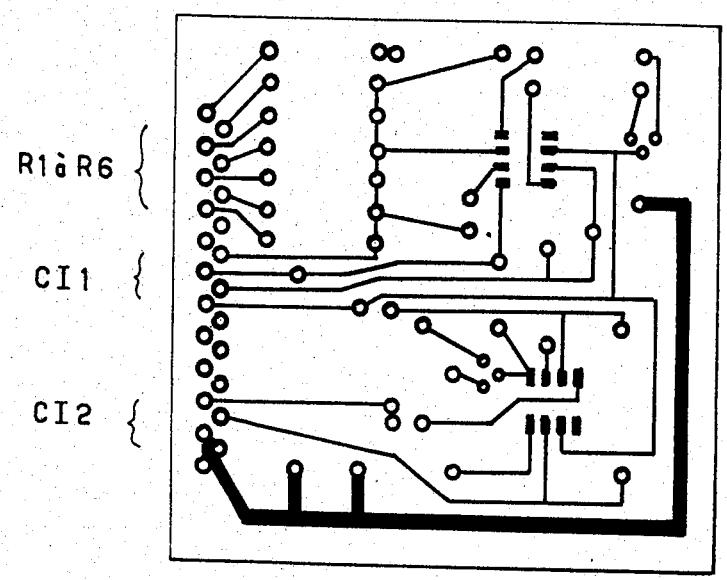
FIG. 4 is a diagram of the components of a photopile amplifier.
Figure 2:
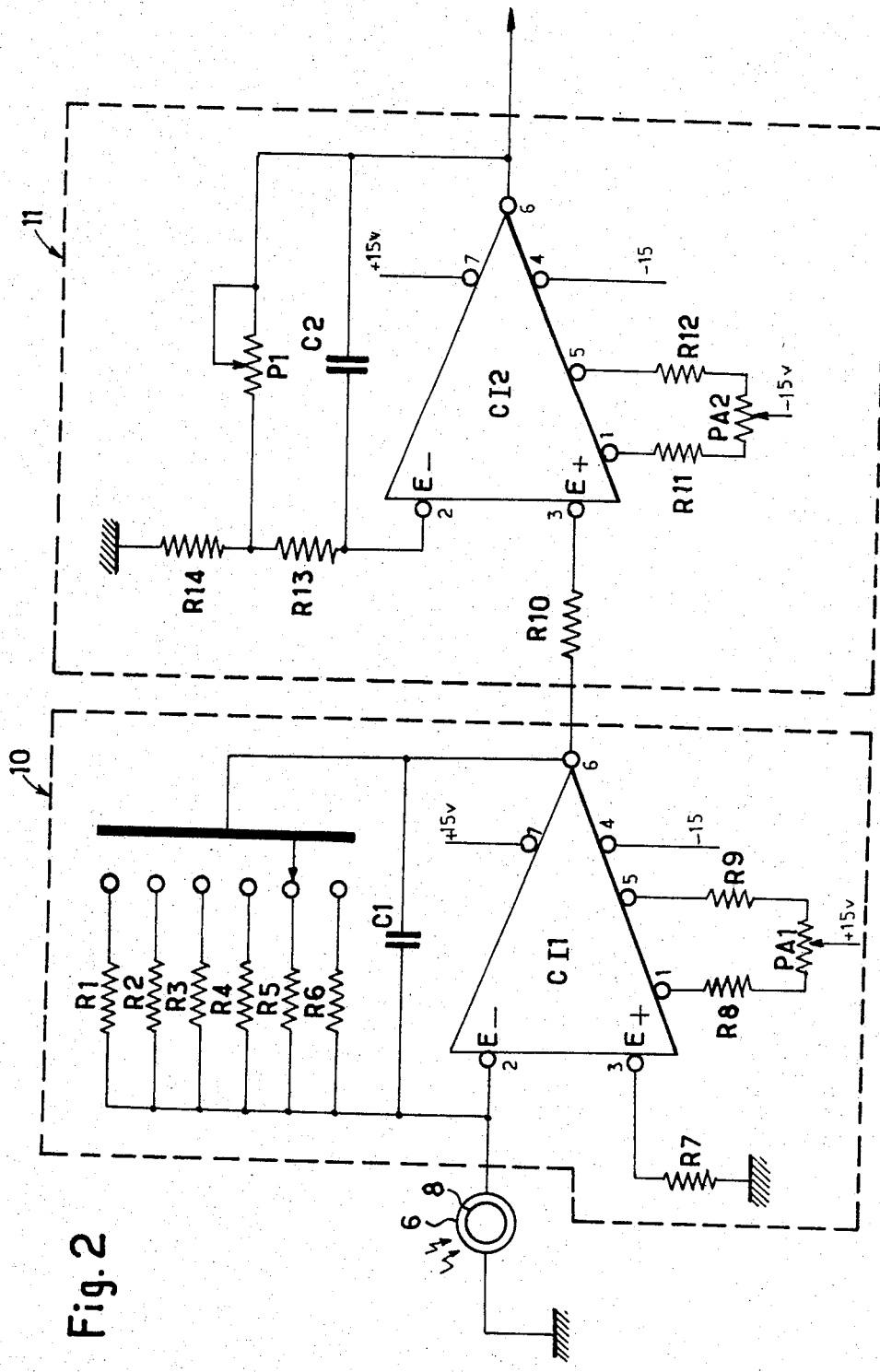
FIG. 2 shows the diagram of the amplifiers of the photopiles.

The photopiles each comprise two integrated operational amplifier stages (see FIGS. 2 and 4). The current delivered by a photopile is proportional to the exciting flux ($S_0$) only if feeding into a low resistance. The first stage 10, connected as a "current-voltage" converter provides this condition. It uses an integrated circuit of the "Bi-fet" type, CI1, and delivers at its output a voltage equal to $E=Ki$, the coefficient K being determined by the load resistor used ($R_1$ to $R_6$). The second stage, 11, uses an integrated circuit connected as a normal voltage amplifier, CI2, whose gain is determined by the resistors $R_{13}$–$R_{14}$ and potentiometer $P_1$.

The outputs 12 and 13 of the respective amplifiers CI2 of the measuring photopile 6 and of the reference photopile 8 feed (see FIG. 3):

into a measuring apparatus, 14 and 15 respectively, through a resistor network 16-17 and 18-19-20 respectively, giving a 5 V standard for the total deviation;

into an output 21 and 22 respectively, for recording, through a resistor network 23-24;

into an input 25 of an analog-digital converter 26, through an amplitude-limiting circuit which ensures protection of the converter and which is formed by a resistor 27 and a Zener diode 28.

The output 29 (on 8 bits) of the analog-digital converter 26 feeds into one of the gates of a microprocessor (as shown schematically in FIG. 3) whereas its output 30 is used for addressing and synchronizing the converter and feeds into the other gate of the microprocessor.

The card of the microprocessor may be designed so as to allow automatic programming of all the operations for measuring the diffusion of the light emitted by a laser ray and diffused through a liquid sample whose turbidity when cold it is desired to check, and the calculation, the integration and the recording of the results, as well as their storage and their comparison with a standard value. Since such a card does not, by itself, come within the scope of the invention, it will not be described and only automatic operations provided by the microprocessor and the combinations of means resulting from this automation will be described.

By varying the values of load resistors $R_1$ to $R_6$ in an appropriate programmed way, it is possible to modify automatically in a programmed way, the sensitivities of the measurements.

Figure 5:
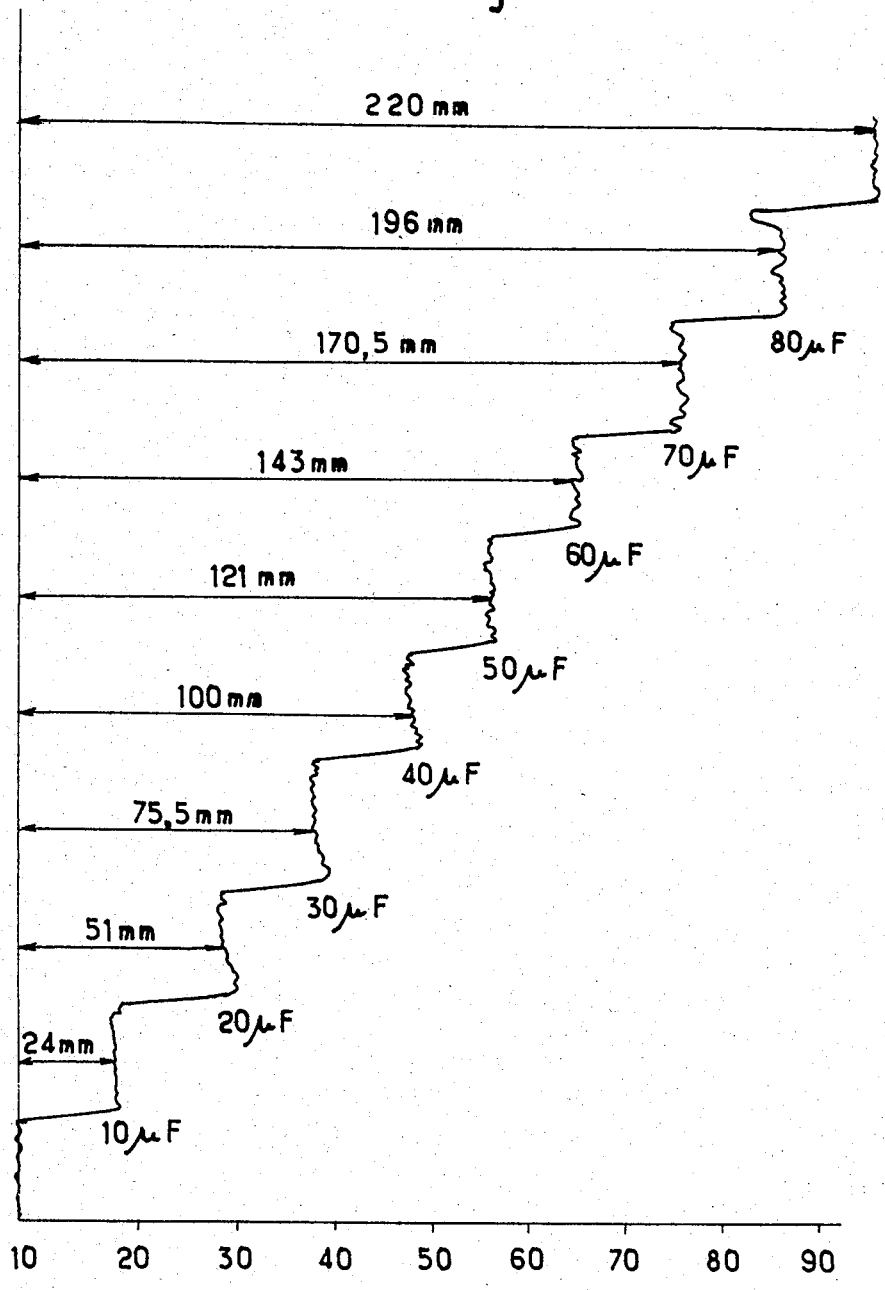
FIG. 5 is a graphic representation of the development of the turbidity of a beer during a measurement (15 minutes), showing the sensitivity of the measurement per formazine unit.

In fact, if we consider for example accompanying FIG. 5, it can be seen that checking the development of the turbidity during a checking handling of a sample, the duration of which is 15 minutes, shows that each of the checks effected approximately every 110 seconds, i.e.

|  | Value in formazine units (UF) | Sensitivity in mm of distance with respect to the origin |
| --- | --- | --- |
| 1st check | 10 UF | 24 mm |
| 2nd check | 20 UF | 51 mm |
| 3rd check | 30 UF | 75.5 mm |
| 4th check | 40 UF | 100 mm |
| 5th check | 50 UF | 121 mm |
| 6th check | 60 UF | 143 mm |
| 7th check | 70 UF | 170.5 mm |
| 8th check | 80 UF | 220.0 mm | shows a practically constant sensitivity of the order of 2.4 for an output voltage of the apparatus of 50 mV and a light flux intensity measured by the reference photopile 8 of 0.66 mA. This sensitivity may be improved, if need be, by appropriately adjusting the values of load resistors $R_1$ to $R_6$.

The following example will show the extreme sensitivity of the measurement effected by laser by means of the apparatus of the invention:

Whereas the alcohol-cold test perfected by CHAPON-CHEMARDIN carried out on KANTERBRAU beer give 1 UF, by nephelometry, using a TEPRAL tank cooled to $-5°$ C. and adding 3% ethanol, the alcohol-cold test used on a KANTERBRAU beer to which 12% ethanol has been added, in an apparatus in accordance with the invention, gives at the end of 15 minutes 80 UF.

Figure 6:
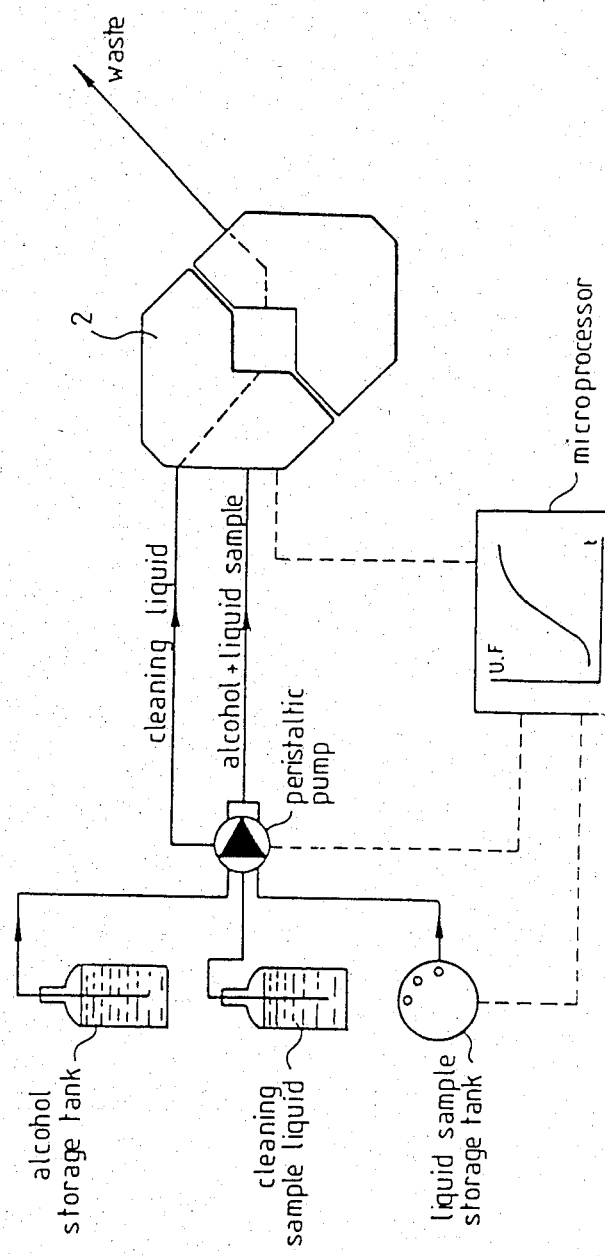
FIG. 6 is a schematic representation illustrating the disposition of the optical system of FIG. 1 relative to systems for introduction of ethanol and for supplying liquid to the sample-holder, and a circuit for cleaning the cooling tank.

By appropriately programming the microprocessor, and by associating with the apparatus of the invention feed-regulating devices for admitting beer samples into the sample-holder cell, as well as feed-regulating devices for introducing ethanol, coupled to an ethanol storage tank and devices for removing the tested samples, it is possible to completely automate the measurement of the colloidal stability of tested liquids. It is also possible to program the periodic cleaning of the sample-holder cell and to print any desired indications (such as the number of the experiment, the result in formazine units, etc.) by means of an associated printer, in accordance with the schematic system diagram of FIG. 6 and the diagram of FIG. 3.

As follows from what has gone before, the invention is in no wise limited to those of its embodiments, modes of application and utilization which have just been described more explicitly; it embraces, on the contrary, all variations thereof which may occur to a man skilled in the art, without departing from the spirit or scope of the invention.

What is claimed is:

1. An apparatus for measuring the colloidal stability of liquids such as nutritional liquids, such as beers, wines and other drinks obtained by fermentation, or gaseous drinks, and oils, in particular, by measuring the diffusion $S_1$ of the light emitted by a helium-neon laser in proportions appropriate for emitting a wavelength of 6328 Å, said apparatus comprising essentially in combination with a laser of said wavelength and with a semitransparent mirror or similar for reflecting a part $S_0$ of an exciting light beam emitted by the laser, in the direction of a reference photopile: a sample-holder containing a sample of the liquid the turbidity of which, when cold, it is desired to measure; a cooling tank which contains the sample-holder and which is associated with a cooling unit of appropriate type; a photopile for analyzing and measuring the light flux from the laser light source, diffused through the sample to be checked; said reference photopile for permanently controlling the intensity of the exciting beam; a logic system associated with a microprocessor, said logic system for cyclically performing the following operations: (a) programmed automatic change of sensitivity, i.e. adjustment of load resistors; (b) standardization allowing a direct measurement in formazine standards; (c) automatic sample handling with the help of a timer internal to the microprocessor; (d) calculation of the quotient $S_1/S_0$ between the two electrical signals corresponding to the scattered flux $S_1$ and the emitted flux $S_0$, received via said two photopiles; and displaying the value of $S_1/S_0$.

2. The apparatus as claimed in claim 1, wherein said photopiles are disposed at an angle of 90° with respect to the emitted light.

3. The apparatus as claimed in claim 2, wherein said photopiles operate at a low voltage and low current, respectively of the order of 50 mV and 0.66 mA, and each comprises two integrated operational amplifier stages the first of which is connected as a "current-voltage" converter which delivers a current proportional to the exciting flux at said low voltage, and the second stage of which is formed by an integrated circuit coupled as a normal voltage amplifier, the outputs of said two amplifiers feeding into a measuring apparatus through a resistor network giving a 50 mV standard for the total deviation, into an output for a recorder through a resistor network and into an input of an analog-digital converter, through an amplitude-limiting circuit which ensures protection of said converter and which is formed by a resistor and a Zener diode.

4. The apparatus as claimed in claim 1, wherein said cooling tank comprises means for establishing a constant cooling temperature, said temperature being adjustable to within 1/10th of a degree.

5. The apparatus according to claim 1, including means for absorbing the nondiffused light.

6. The apparatus as claimed in claim 1, wherein a system is provided for supplying the sample-holder with samples, including a feed-regulating programmed automatically controlled peristaltic pump, which takes the liquid from a storage tank, and transfers it to the sample-holder cells in desired proportions.

7. The apparatus as claimed in claim 6, wherein said peristaltic pump takes the liquid directly from manufacturing tanks.

8. The apparatus as claimed in claims 6 or 1, wherein the automatic programmed introduction of samples of liquid to be checked and ethanol into the sample-holder cells is achieved with the help of said microprocessor.

9. The apparatus as claimed in claim 1, wherein there is provided a system for introducing ethanol into the liquid to be tested before its introduction into the sample-holder cells, including a feed-regulating programmed, automatically controlled peristaltic pump means having an electromagnetic valve for introducing the ethanol contained in a storage tank associated with the apparatus into the liquid to be tested in desired proportions said proportions being determined with the aid of a timer internal to the micro-processor.

10. The apparatus as claimed in claim 1, wherein means are provided for adjusting the sensitivity of the measurement, said means being controlled automatically and programmed by the microprocessor and comprising load resistors.

11. The apparatus as claimed in claim 1, wherein there is further provided a circuit for the circulation of liquids for cleaning the cooling tank and the sample-holder cells, controlled and programmed by the microprocessor.

12. The measuring method as claimed in claim 1 including automatic programming of all the operations for measuring the diffusion of the light emitted and diffused through the sample of liquid to be checked, and the calculation, the integration and the recording of the results, as well as their storage and their comparison with the standard curve.

13. A method for measuring the colloidal stability of liquids, particularly nutritional liquids, and more particularly beers, consisting in providing a sample of beer of which it is desired to check the turbidity when cold, adding a quantity of ethanol to the sample of up to 12% in volume with respect to the volume of the beer providing cellular apparatus for containing said resulting sample and cooling said sample to a temperature of the order of $-8°$ C. practically instantaneously on its entry into the apparatus, the capacity of the cells containing the sample being of the order of 150 $\mu$l, so as to obtain maximum turbidity after 15 minutes directing a laser ray emitted at a wavelength of 6328 Å at said sample; measuring diffusion of the light flux ($S_1$) by a photopile placed at 90° with respect to the emission direction of the laser ray, converting the light flux signal into a current-voltage signal and transmitting said current-voltage signal to a microprocessor; directing a part of the light flux reflected by a semitransparent mirror towards a reference photopile also placed at 90°; simultaneously measuring the intensity of the emitted light flux ($S_0$) and transmitting the corresponding signal to the microprocessor; calculating the ratio $S_1/S_0$ via the microprocessor to eliminate the fluctuations in intensity of the laser; displaying the value of $S_1/S_0$ obtained which, after comparison with a standard curve established by means of a formazine solution and integrated by the microprocessor, is expressed directly in formazine units (UF); and establishing and recording a curve of sensitivity as a function of the UF reading.

* * * * *